(12) United States Patent
Proctor et al.

(10) Patent No.: US 8,138,480 B2
(45) Date of Patent: Mar. 20, 2012

(54) BULK MATERIAL ANALYZER ASSEMBLY INCLUDING STRUCTURAL BEAMS CONTAINING RADIATION SHIELDING MATERIAL

(75) Inventors: Raymond John Proctor, San Diego, CA (US); Anton Mario Lucchin, San Marcos, CA (US); Thomas Leland Atwell, Camp Verde, AZ (US); Mark Rudy Chiesman, Ramona, CA (US)

(73) Assignee: Thermo Fisher Scientific Inc., Waltham, MA (US)

( * ) Notice: Subject to any disclaimer, the term of this patent is extended or adjusted under 35 U.S.C. 154(b) by 543 days.

(21) Appl. No.: 12/376,839

(22) PCT Filed: Aug. 10, 2007

(86) PCT No.: PCT/US2007/017780
§ 371 (c)(1),
(2), (4) Date: Feb. 9, 2009

(87) PCT Pub. No.: WO2008/021228
PCT Pub. Date: Feb. 21, 2008

(65) Prior Publication Data
US 2010/0163734 A1    Jul. 1, 2010

Related U.S. Application Data

(60) Provisional application No. 60/837,083, filed on Aug. 11, 2006.

(51) Int. Cl.
*G01N 23/222* (2006.01)
(52) U.S. Cl. .................................... 250/359.1
(58) Field of Classification Search ............... 250/358.1, 250/359.1, 360.1
See application file for complete search history.

(56) References Cited

U.S. PATENT DOCUMENTS

| | | | |
|---|---|---|---|
| 4,929,895 A | 5/1990 | Typpo | |
| 5,124,554 A * | 6/1992 | Fowler et al. | 250/358.1 |
| 5,315,124 A | 5/1994 | Goss et al. | |
| 5,396,071 A | 3/1995 | Atwell et al. | |
| 5,539,788 A | 7/1996 | Ruddy et al. | |
| 5,732,115 A | 3/1998 | Atwell et al. | |
| 6,157,034 A | 12/2000 | Griebel et al. | |

(Continued)

FOREIGN PATENT DOCUMENTS
SU    984491    12/1982
(Continued)

*Primary Examiner* — David Porta
*Assistant Examiner* — Marcus Taningco
(74) *Attorney, Agent, or Firm* — Edward W. Callan (57) ABSTRACT

A bulk material analyzer (FIG. 2) is variably constructed from an assembly of components The analyzer (FIG. 2) is the type that is used to analyze bulk material (28) transported on a conveyor belt (29) through an activation region (30) between at least one radiation source (element 11) and at least one radiation detector (12) within the bulk material analyzer (FIG. 2) The assembly includes a radiation-source box (11) for disposition either above the activation region (30) or below the conveyor belt (29), a radiation-detector box (12) for disposition on the opposite side of the activation region (30) and the conveyor belt (29) from the radiation-source box (11); and a set of stackable structural beams (14, 15, 16, 17, 18, 19) predominantly containing radiation shielding material and configured for stacking about the activation region (30), the radiation-source box (11) and the radiation-detector box (12) to prevent unwanted radiation being generated and transported to the radiation-detector box (12).

20 Claims, 4 Drawing Sheets

U.S. PATENT DOCUMENTS

| | | |
|---|---|---|
| 6,470,285 B1 | 10/2002 | Atwell et al. |
| 6,657,189 B2 | 12/2003 | Atwell et al. |
| 2002/0196890 A1* | 12/2002 | Shimizu et al. ............... 376/273 |
| 2005/0077471 A1* | 4/2005 | Edwards et al. ........... 250/360.1 |
| 2009/0101827 A1* | 4/2009 | Harris et al. ............... 250/360.1 |

FOREIGN PATENT DOCUMENTS

| WO | WO 97/43625 | 11/1997 |
|---|---|---|

* cited by examiner

BULK MATERIAL ANALYZER ASSEMBLY INCLUDING STRUCTURAL BEAMS CONTAINING RADIATION SHIELDING MATERIAL

CROSS-REFERENCE TO RELATED APPLICATION

"The present application claims the benefit of co-pending U.S. provisional patent application No. 60/837,083 filed Aug. 11, 2006, which is incorporated herein by reference in its entirety.

BACKGROUND OF THE INVENTION

The present invention generally pertains to bulk material analyzers and is particularly directed to an improved assembly of components for constructing a bulk material analyzer of the type that is used to analyze bulk material transported on a conveyor belt through an activation region located in a tunnel between at least one radiation source and at least one radiation detector within the bulk material analyzer.

Bulk material analyzers are used to measure the elemental content of bulk materials. In one type of bulk material analyzer, the radiation source includes one or more neutron sources and the radiation detector includes one or more gamma ray detectors that produce signals which are processed to provide a measurement of the elemental content of the bulk material. When the bulk material is bombarded with neutrons, emissions of gamma rays are produced from the bulk material. Different characteristic spectra of gamma ray energy are produced from different elements of the bulk material. By processing the detected signals that are indicative of the gamma ray spectrum a measurement is provided of the elemental content of the bulk material. This measurement process is known as prompt gamma ray neutron activation analysis (PGNAA). In addition to containing the radiation source and the radiation detector, the bulk material analyzer assembly necessarily includes a large quantity of radiation shielding material in order to protect persons using the bulk material analyzer from harmful doses of radiation. As used herein the term "radiation shielding material" means material that absorbs, scatters, attenuates and/or reflects neutron radiation and/or gamma radiation. The required quantity of radiation shielding material is such that some embodiments of the bulk material analyzer assembly are so large that the assembly is not easily handled for transportation from one site to another.

U.S. Pat. No. 5,396,071 to Atwell et al. describes a modular assembly for a PGNAA bulk material analyzer of the type in which bulk material is transported on a conveyor belt through an activation region located between at least one radiation source and at least one radiation detector within the bulk material analyzer. Such assembly includes container means that include a lower primary module containing radiation shielding material and defining either at least one radiation source cavity or at least one radiation detector cavity; and an upper primary module containing radiation shielding material and defining the other of either the at least one radiation source cavity or the at least one radiation detector cavity that is not defined by the lower primary module. The lower primary module and the upper primary module are so shaped that the passageway is delimited by placement of the upper primary module upon the lower primary module; and portions of the lower primary module are shaped for delimiting the sides of a trough that is contoured for accommodating passage of the conveyor belt through the activation region. The trough-delimiting portions of the lower module are inclined outwardly from the bottom of the passageway to accommodate a passage on a conveyor belt having a complementary contour.

The modular assembly described in the aforementioned U.S. Pat. No. 5,396,071 is easily handled for transportation and readily installed about a conveyor belt that is used for transporting the bulk material that is to be analyzed, such that the analyzer can be installed in an existing processing line without having to cut or otherwise disassemble the conveyor belt. As the so-described modular assembly has been applied to a wide range of applications, it has been found that a given embodiment thereof can be used with only small ranges of conveyor belt sizes and shapes. Although small differences in conveyor belt sizes and shapes have been compensated for by placing neutron-moderating-material liners of selected sizes and shapes on the respective modules adjacent the passageway, when such differences are not small it has been necessary to provide an entirely different bulk material analyzer assembly including a passageway and a trough having dimensions and shapes that are appropriate for accommodating the passage of the conveyor belt.

U.S. Pat. No. 6,157,034 to Griebel et al. describes a flexible modular assembly for a bulk material analyzer that can be modified for use with large ranges of conveyor belt sizes and shapes. The assembly includes a first module containing radiation shielding material and at least one radiation source; second module containing radiation shielding material and including at least one radiation detector; and at least two replaceable modules, each containing radiation shielding material, sandwiched between the first module and the second module to separate the first module from the second module, with the at least two replaceable modules being separated, to delimit a tunnel for movement of the bulk material through the activation region.

It is also known to install a PGNA bulk material analyzer by removing a section of an existing conveyor belt and conveyor support structure and installing the analyzer in the gap thus created in the conveyor support structure. This technique eliminates all conveyor belt support structural materials from the analysis volume and prevents extraneous signals from contaminating the analysis. However, use of this technique incurs considerable expenses in mechanical, civil and electrical engineering to redesign and rebuild the weakened conveyor support structure and to support the analyzer.

SUMMARY OF THE INVENTION

The present invention provides an assembly of components for constructing a bulk material analyzer of the type that is used to analyze bulk material transported on a conveyor belt through an activation region located in a tunnel between at least one radiation source and at least one radiation detector within the bulk material analyzer, said assembly comprising: a radiation-source box for disposition either above the activation region or below the conveyor belt; a radiation-detector box for disposition either below or above the radiation source box on the opposite side of the activation region and the conveyor belt from the radiation-source box; and a set of stackable structural beams predominantly containing radiation shielding material and configured for stacking about the activation region, the radiation-source box and radiation-detector box to prevent unwanted radiation being generated and transported to the radiation-detector box when said boxes are disposed on opposite sides of the activation region and the conveyor belt from each other; wherein said assembly can be used to construct a bulk material analyzer that can be mounted directly on an existing conveyor support structure, without removing or substantially modifying any part of the existing conveyor support structure.

The present invention also provides a bulk material analyzed constructed with the above-described assembly of components.

This assembly of components can be adapted to different conveyor belt support structures and is sufficiently flexible to allow a user to change the disposition of the components in the field.

The assembly of bulk material analyzer components according to the present invention can be used to construct a bulk material analyzer that is relatively small and light. The structural beams containing radiation shielding material are dimensioned for ease of mounting, are structurally strong, and are disposed to provide good neutron radiation shielding to thereby minimize the production of unwanted gamma ray signals and are long lived in an industrial environment.

The structural beams containing radiation shielding material preferably are disposed to attenuate all leakage paths that allow neutrons to reach the conveyor support structure or other background materials, by substantially surrounding the source of neutrons and the analysis volume with strategically located neutron-absorbing shields. The analyzer has many other novel features that optimize practical field performance and enable configuration changes in the field to be performed by an operator.

Additional features of the present invention are discussed in the detailed description of the various embodiments.

DETAILED DESCRIPTION

Figure 1:
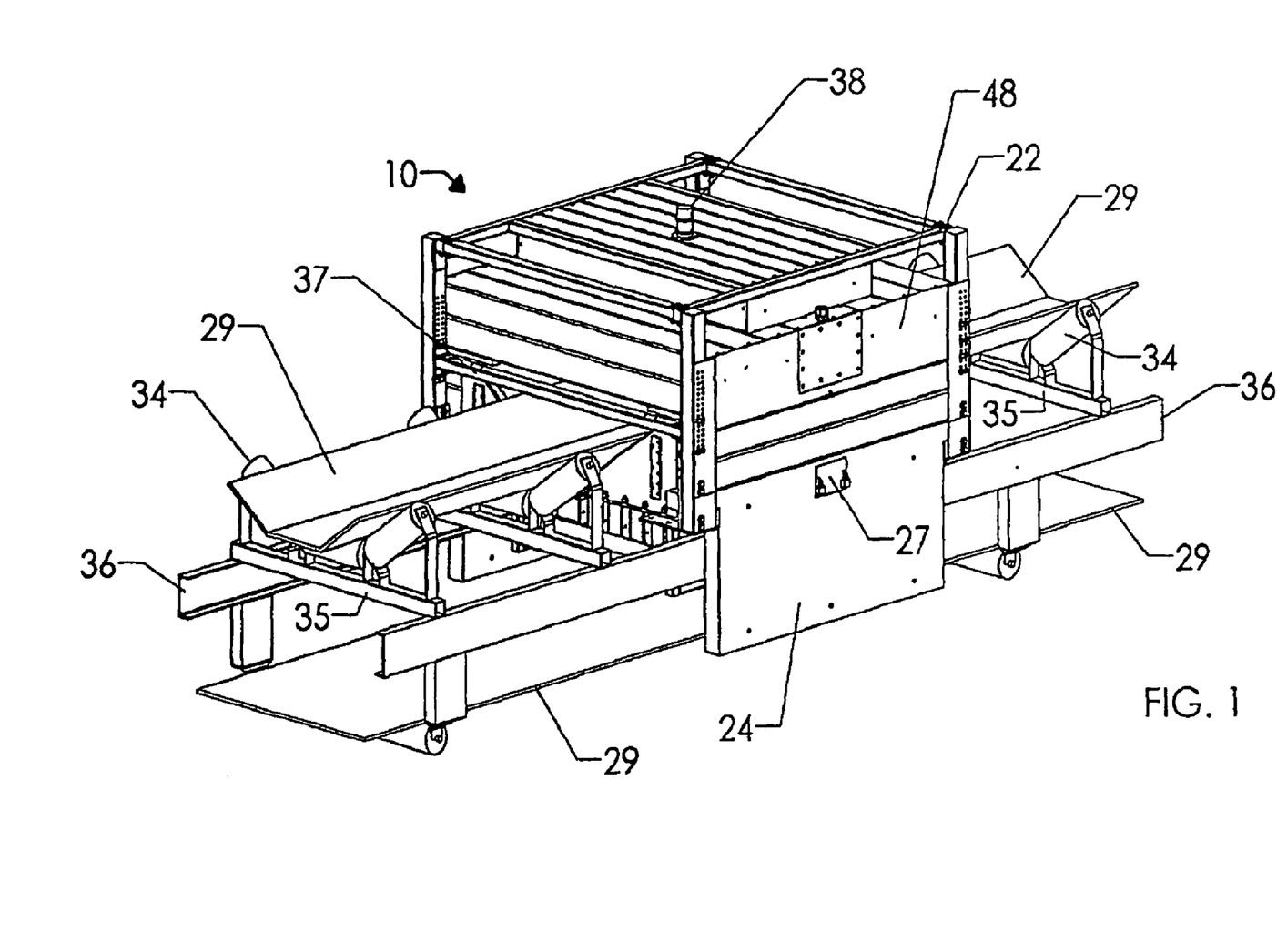
FIG. 1 is a perspective view of an embodiment of a bulk material analyzer constructed with an assembly of components according to the present invention, wherein the radiation source box is disposed below and the radiation detector box is disposed above the activation region.
Figure 2:
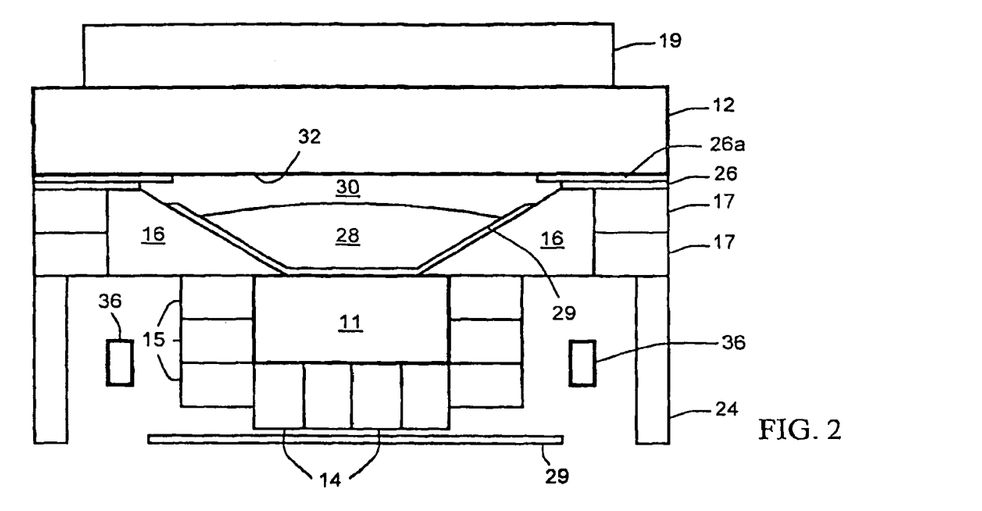
FIG. 2 is a sectional view taken along line 2-2 in FIG. 3 showing the disposition of the assembled components in the analyzer of FIG. 1.
Figure 3:
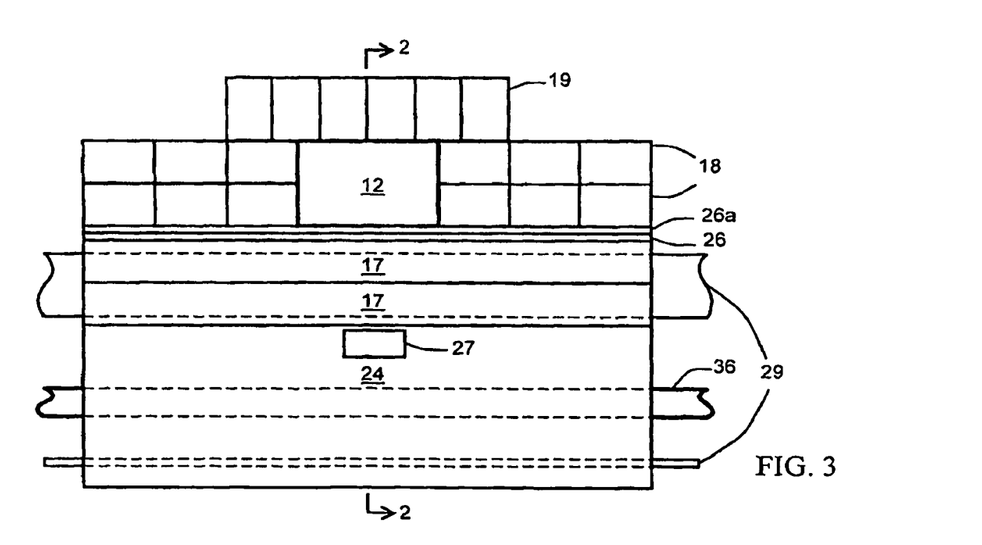
FIG. 3 is a side elevation view showing the disposition of the assembled components in the analyzer of FIG. 1 in an embodiment including one radiation detector box.

Referring to FIGS. 1, 2 and 3, one embodiment of a bulk material analyzer 10 constructed with an assembly of components according to the present invention includes a radiation source box 11, a radiation detector box 12, a set of stackable structural beams 14, 15, 16, 17, 18, 19, a rigid frame 22, side shields 24 and spacer sheets 26, 26a.

These components are light enough and of such dimensions that they can be carried by laborers for installation in places where cranes, forklifts and other forms of mechanical assistance cannot be used, such as around conveyors in tunnels and other places where access is restricted, for example.

The radiation-source box 11 contains at least one receptacle for neutron source material. Typically the neutron source material is inserted into the radiation-source box 11 through a hatch 27 in the side shield 24 after the bulk material analyzer 10 has been constructed. The radiation-source box 11 also contains radiation shielding material disposed about the neutron-source-material receptacle(s). The radiation-source box 11 is dimensioned to accommodate isotopic or neutron generation neutron sources and to be stackable with the structural beams 14, 15, 16, 17, 18, 19. In an alternative embodiment (not shown), two or more radiation-source boxes 11 are disposed side-by-side.

The radiation detector box 12 includes one or more gamma ray detectors that produce signals which are processed to provide a measurement of the elemental content of the bulk material. The radiation detector box 12 also includes radiation shielding material disposed between the gamma ray detector(s) and the ends of the box 12. The radiation-detector box 12 is dimensioned to accommodate one or more detectors and to be stackable with the structural beams 14, 15, 16, 17, 18, 19.

The structural beams 14, 15, 16, 17, 18, 19 contain predominantly radiation shielding material. A majority of the structural beams 14, 15, 17, 18, 19 are interchangeable.

The assembly of components is used to construct a bulk material analyzer of the type in which the bulk material 28 is transported on a conveyor belt 29 through an activation region 30 located in a tunnel 32 between at least one radiation source and at least one radiation detector within the bulk material analyzer. In this embodiment, when the bulk material analyzer 10 is being used, at least one radiation source is contained within the radiation-source box 11, which is disposed below the conveyor belt 29, and at least one radiation detector is contained within the radiation-detector box 12, which is disposed above the activation region 30 on the opposite side of the activation region 30 and the conveyor belt 29 from the radiation-source box 11. The conveyor belt 28 is supported by a conveyor-support structure, which includes rollers 34 disposed on cross-members 35 that extend between a pair of rails 36.

The set of stackable structural beams 14, 15, 16, 17, 18, 19 is configured for stacking about the activation region 30, the radiation-source box 11 and radiation-detector box 12 to prevent unwanted radiation from being generated and transported to the radiation-detector box 12 when the boxes 11, 12 are disposed on opposite sides of the activation region 30 and the conveyor belt 29 from each other 12, 11.

In one embodiment, the structural beams 14, 15, 16, 17, 18, 19 are made from structural fiber reinforced plastic (FRP) hollow tubes, which are filled with borated radiation shielding materials. FRP is resistant to moisture, corrosion, insects, fungi, temperature extremes & sunlight in an industrial environment for periods exceeding the ten-year design life of most analyzers. The tube cross section has tight tolerances and allows stacking with minimal gaps.

In one embodiment, the fiber reinforcing material is E-glass, which is a borosilicate glass with 8-13% $B_2O_3$. $B_2O_3$ absorbs neutrons and suppresses gamma rays produced from the FRP materials.

The radiation shielding material is designed for use with both Cf-252 and a neutron generator.

The radiation shielding materials are selected to be highly hydrogenous, such as, for example; polyethylene; polypropylene & wax, in order to stop fast neutrons. The radiation shielding materials can also contain neutron poisons like Boron and Lithium to suppress gamma ray production in the structural beams 14, 15, 16, 17, 18, 19.

In another embodiment, the structural beams 14, 15, 16, 17, 18, 19 are solid plastic beams. Although rigid some solid plastic structural beams could sag over the lifetime of a PGNA bulk material analyzer, the use of plastic beams reinforced with borosilicate fibers both strengthens the beam and suppresses the gamma ray production from the structural beams 14, 15, 16, 17, 18, 19. The use of re-cycled plastic is especially appealing.

The structural beams 14, 15, 16, 17, 18, 19 can be stacked and are strong enough that they can be bolted together at the ends. FRP end caps seal and strengthen the ends of the structural beams 14, 15, 16, 17, 18, 19. Any damaged piece can be easily replaced at low cost.

In the preferred embodiment the structural beams 14, 15, 17, 18, 19 are rectangular for easy filling and efficient stacking. Alternatively triangular, square, hexagonal or other stackable beam cross sections can be used. Round beams also can be used if the voids between the beams are filled. Alternately the round beam thickness can be increased to compensate for missing radiation shielding material in the voids.

The structural nature of the structural beams 14, 15, 16, 17, 18, 19 allows structural steel members of the bulk material analyzer 10, such as the frame 22, to be disposed far enough away from the regions of high neutron flux as to minimize any production of extraneous gamma rays so that the detected gamma ray spectrum results predominantly from the bulk material 28 on the conveyor belt 29 and not the supporting structure of the analyzer 10.

The length of the structural beams 14, 15, 16, 17, 18, 19 is variable and is determined by the size of bulk material analyzer 10 being constructed. In a preferred embodiment the structural beams 14, 15, 17, 18, 19 are commercial continuously pultruded, rectangular FRP tubes cut to the desired length.

In one embodiment the structural beams 14, 15, 17, 18, 19 have a 3:2 width-to-height ratio. This provides flexibility in the stacking of the beams to allow a desired unit thickness of radiation shielding in a range including 2, 3, 4, 5, 6 . . . etc. In one such embodiment, the structural beams 14, 15, 17, 18, 19 have a rectangular cross section of six inches-by-nine inches. In other embodiments width-to-height ratio is 1:1, 1:2, 1:3, etc, to allow 1, 2, 3, 4, 5, 6 . . . , etc. unit thick radiation shielding.

The frame 22 is mounted directly on the rails 36 of the conveyor support structure, without removing or substantially modifying any part of the existing conveyor support structure. The frame 22 is used to support the ends of at least some of the stacked structural beams 14, 15, 16, 17, 18, 19 and the ends of the radiation-source box 11 and radiation-detector box 12 as the bulk material analyzer 10 is assembled about an in-situ conveyor belt 29 and conveyor belt support system from the bottom up by stacking the structural beams 14, 15, 16, 17, 18, 19 about the activation region 28, the radiation-source box 11 and radiation-detector box 12.

Advantages provided by mounting the frame 22 directly on the rails 36 of the conveyor support structure include (a) being able to construct the analyzer about a conveyor belt support system that inclined up to approximately twenty degrees from the horizontal, (b) more resistance to vibration and abuse, (c) easier replacement of a damaged structural beam 14, 15, 16, 17, 18, 19, and (d) easier raising of the top portion of the analyzer 10 above the activation region 30 when adjusting the height of the tunnel 32.

In the preferred embodiments, the rigid frame 22 is made of steel, aluminum or other structural metal. Mounting of the frame 22 to the rails then involves fastening metal to metal by bolts, welding, etc.

In an alternative embodiment, the frame 22 is made of FRP or some other composite for lightness.

The number of structural beams 14, 15, 16, 17, 18, 19, which are stacked and secured to the frame can be varied for optional flexible tailoring of the disposition of radiation shielding material. Fewer structural beam 14, 15, 16, 17, 18, 19 are used when neutron source intensities are much less than the nominal, whereby the analyzer is lighter but may provide a lower performance. Optionally if more detectors are used then performance is not reduced. More structural beam 14, 15, 16, 17, 18, 19 are used when a neutron generator with more penetrating neutrons is used.

In an alternative embodiment (not shown) the structural beams are mounted directly on the rails 36 of the conveyor support structure.

Some of the structural beams 15 containing radiation shielding material are dimensioned so that they 15 can be disposed parallel to the longitudinal axis of the conveyor belt 29 and laterally between the radiation-source box 11 and the conveyor support structure 34, 35, 36 when the radiation source box 11 is disposed below the conveyor belt 29 to reduce the problem of gamma rays emitted from the conveyor support structure 34, 35, 36 interfering with. PCNA analysis of the material 28 on the conveyor belt 29.

The physical constraints of mounting a PGNA bulk material analyzer on the conveyor support structure have led some manufacturers to locate the majority of the radiation protection shielding material outside the confines of the rails 36. This leaves the belt rails and all structural elements exposed to a flux of neutrons emitted by the analyzer's neutron source(s). The conveyor support structure normally incorporates various alloys of steel, enclose electrical conduits, carry air and water lines, and often lie in close proximity to either a concrete floor or the ground.

Unfortunately, gamma ray attenuating materials also emit their own interfering gamma ray signatures when exposed to neutrons. These unwanted signals contaminate the useful signals from the materials of interest in the activation region of the PGNA analyzer. Neutrons from PGNA analyzers mounted over the conveyor support structure will excite, for example, strong gamma ray signals from both the Iron in the structural steel, the Copper in the service conduits, and the Silicon, Aluminum, Calcium, and Iron from the ground. These unwanted background signals, if unsuppressed, will contaminate the gamma ray emissions from the materials 28 of interest on the conveyor belt 29 and thereby degrade the analysis.

The radiation shielding material in the structural beams 15 that are disposed between the radiation-source box 11 and the conveyor support structure 34, 35, 36 attenuate all leakage paths that might allow neutrons to reach the conveyor support structure or other background materials, whereby any resultant excitation of gamma rays from the conveyor belt structure is prevented. For example, 15 mm of dense radiation shielding materials like Lead or Bismuth attenuate only 50% of 5-Million Electron Volt (MeV) gamma rays. A reduction of the gamma ray flux to less than one-eighth of the unattenuated value requires more than 50 mm of such gamma ray shielding material.

Use of 50 mm of highly hydrogenous shield materials like Polyethylene, Polypropylene, or Wax as radiation shielding material in the structural beams 15 attenuates approximately 50% of fast neutrons. A reduction of the neutron flux to ½×½×½=⅛th of its unshielded value requires shielding of 50+50+50 mm=150 mm of such hydrogenous shields or their equivalent. Maintaining such thick radiation shielding between regions of high neutron flux and the structural and surrounding elements prevents the excitation of gamma rays that would interfere with the material analysis. The use of neutron poisons in the fast neutron radiation shielding material, such as Boron, Lithium, etc., reduces the emission of Hydrogen gamma rays from the shielding material.

Neutron generator 14 MeV neutrons from a DT reaction are more penetrating than Cf-252 neutrons as shown in Table 1.

TABLE 1

Neutron Flux levels in Steel Belt Rails for $1 \times 10^8$ neutrons/sec

| Neutrons | n/cm2/sec Cf-252 | n/cm2/sec DT | DT/Cf Ratio | mm of extra Shield for DT |
|---|---|---|---|---|
| Thermal (<0.1 eV) | 8 | 10 | 1.3 | 17.6 |
| Epithermal (0.1-$10^5$ eV) | 25 | 878 | 35 | 261.5 |
| Fast (>$10^5$ eV) | 40 | 1967 | 49 | 285.7 |

Hence to match the epithermal neutron flux levels of an isotopic Cf-252 neutron source system a DT generator system requires more than 250 mm of extra shielding. This extra shielding is possible when the conveyor belt is wide and there is more space between the belt rails. This is more difficult with smaller belts, but some belt structure shielding can be achieved by using extremely efficient neutron shielding material, such as pure polyethylene.

Another method for reducing the problem of gamma rays being emitted from the conveyor support structure problem is to paint the conveyor support structure with neutron absorbing paint to suppress the absorption of thermal neutron flux. Examples include Boron/Epoxy or Lithium/Epoxy paint. A 0.05 mm-thick layer of Boron attenuates approximately 50% of the thermal neutrons. A reduction of an incoming thermal flux to less than one-eight of the unattenuated value requires more than 0.4 mm of 50% borated Epoxy paint. This method can help if structural elements are very thin and are only excited by externally produced thermal neutrons. But it does not eliminate signals from epithermal neutron reactions, for example the 25 keV resonance from Iron in steel. It also does not limit thermal neutrons produced internally in the structural members by fast neutrons because only thick hydrogenous shields reduce fast neutrons. Thus, to attenuate all neutron fluxes to one-eighth would require hydrogenous epoxy paint several centimeters thick.

In one embodiment, structural beams 14, 15 providing at least 150 mm of borated polyethylene as the radiation shielding material are disposed around the radiation-source box 11 to attenuate the neutrons leaking out of the neutron-emitting region by at least a factor of 8. This embodiment reduces the gammas rays emitted by the conveyor support structure by a factor of 8, which is so low that the signature of such emitted gamma rays is not detected in the analysis of the material on the belt.

The structural beams 14, 15 also minimize the neutron flux in the ground or a concrete floor below the conveyor support structure.

The side shields 24 contain predominantly radiation shielding material. The side shields 24 are disposed outside the conveyor-support structure 34, 35, 36 to reduce the neutron fluxes at the sides of the analyzer with respect to the longitudinal axis of the conveyor belt 29 where workers may pass close by the analyzer. The side shields 24 provide biological shielding that is necessary when strong 2.times.10.sup.8 neutron/sec neutron sources are mounted underneath the activation region 30.

The thickness of the side shields 24 is optimized for the more penetrating radiation of a neutron generator, which allows an analyzer to be shipped with isotopic neutron sources e.g. Cf-252, and to be field upgradeable to a neutron generator without having to change the side shield. Individual side shields 24 include up to eight one-inch thick polypropylene sheets. For small belts where six-inch thick side shields are required structural beams 14, 15, 17, 18, 19 can be stacked to provide the side shielding outside the conveyor support structure.

Some of the structural beams 16 are configured for defining a trough adjacent the activation region 30 for supporting the conveyor belt 29 in a trough-like configuration. In some embodiments (not shown) the trough-defining beams 16 are stacked together to attain a desired height.

In some embodiments of the assembly of components, some of the trough-defining beams 16 define a trough having side walls that are inclined at a first predetermined troughing angle; and some of the trough-defining beams 16 define a trough having side walls that are inclined at a second predetermined troughing angle that is other than the first predetermined troughing angle. In one embodiment, troughing angles of 20, 25, 30, 35, 40 and 45 degrees are defined by different pairs of trough-defining beams 16.

Trough-defining beams 16 that define one predetermined troughing angle are interchangeable with trough-defining beams 16 that define a different predetermined troughing angle. This feature is advantageous for situations when it is desirable to vary the troughing angle in accordance with the cross-sectional area of the bulk material that is being analyzed. For example, initially a shallow belt troughing angle, such as 20 degrees, will allow the detectors to be closer to the bulk material 28 on the belt 29 for a more sensitive analysis when the cross-sectional area is relatively small and then switched to a deeper troughing angle, such as 35 degrees, when the cross-sectional area is larger.

In other embodiments the trough-defining beams 16 that are included in the assembly of components define a trough having side walls that are inclined at only a single predetermined troughing angle.

The spacer sheets 26, 26a contain predominantly radiation shielding material. The spacer sheets 26, 26a are disposed between some of the stackable structural beams 17, 18 for adjusting the height of the tunnel.

Conveyor belts can carry bulk materials ranging in particle sizes from powder to larger than 300 mm boulders. When an analyzer is first specified the tunnel clearance is optimized to be the lowest compatible with clearing the highest practical belt loading. However, in years of operation as the mining/quarry operation evolves the particle sizes and material bed depths can change. To accommodate this variation the tunnel height clearance above the belt can be varied in the field by varying the number of spacer sheets 26, 26a that are disposed between some of the stackable structural beams 17, 18.

The spacer sheets 26, 26a extend the length of the analyzer on both sides at the top of the tunnel 32. The spacer sheets 26, 26a support some of the upper shielding beams 18.

In one embodiment the spacer sheets 26, 26a are one-inch thick polypropylene sheets so that the tunnel height can be adjusted in one-inch steps. Other thicknesses can be used.

Field adjustment of the tunnel height is possible because the rigid structural beams 18 in the roof of the tunnel 32 are strong enough to allow the use of external hydraulic jacks for raising and lowering the roof whilst spacers are added or removed.

Even though the structural beams 18 are very strong and can be replaced if damaged, a preferred embodiment also includes a replaceable steel crash bar 37, which is disposed over the entrance to the tunnel 32 to take the initial impact of any oversize material on the conveyor belt 29. The height of the crash bar is also height adjustable by varying its position on the frame 22 to always protect the roof of the tunnel 32.

At least some of the spacer sheets 26a are dimensioned for disposition adjacent the edges of the conveyor belt 29 for being contacted by the edges of the conveyor belt when the conveyor belt is significantly misaligned. These spacer sheets 26a act as sacrificial materials that can be abraded away by the edge of a misaligned belt and thereby prevent any damage to the radiation detector box 12. These spacer sheets 26a can be easily replaced during routine service. The degree of penetration of these spacer sheets 26a into the belt tunnel determines the probability of these spacer sheets 26a being impacted by a misaligned conveyor belt 29.

When a neutron generator is used, there is a lamp 38 on the top of the analyzer 10 for indicating when the radiation source is generating neutrons.

Cosmetic side panels 48 are disposed on the upper sides of the analyzer 10.

The embodiment of FIGS. 1, 2 and 3 is used primarily for analysis of mining materials that have a low Hydrogen content, and is also useful for analysis of materials.

Figure 4:
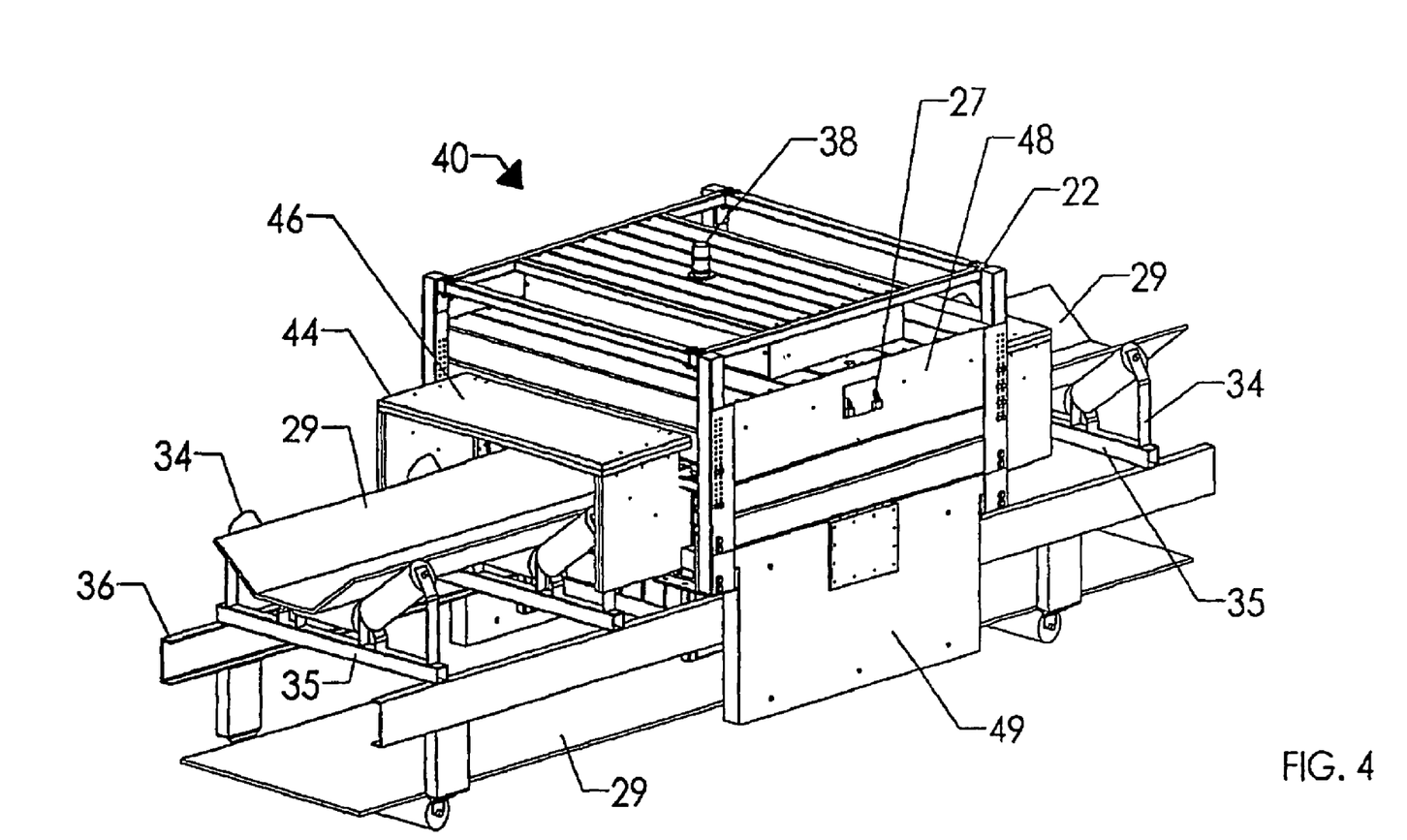
FIG. 4 is a perspective view of an embodiment of a bulk material analyzer constructed with an assembly of components according to the present invention, wherein the radiation source box is disposed above and the activation and the radiation detector box is disposed below the activation region.
Figure 5:
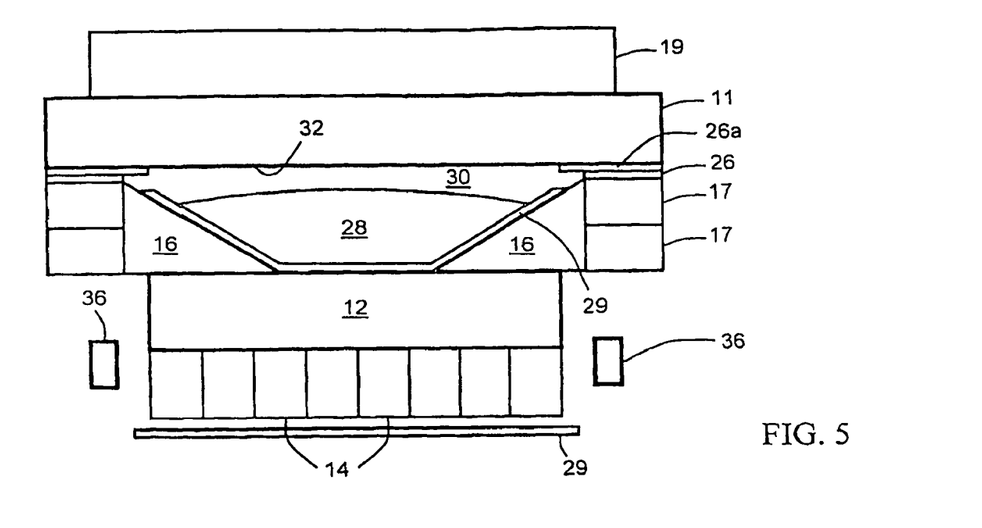
FIG. 5 is a sectional view taken along line 5-5 in FIG. 6 showing the disposition of the assembled components in the analyzer of FIG. 4.
Figure 6:
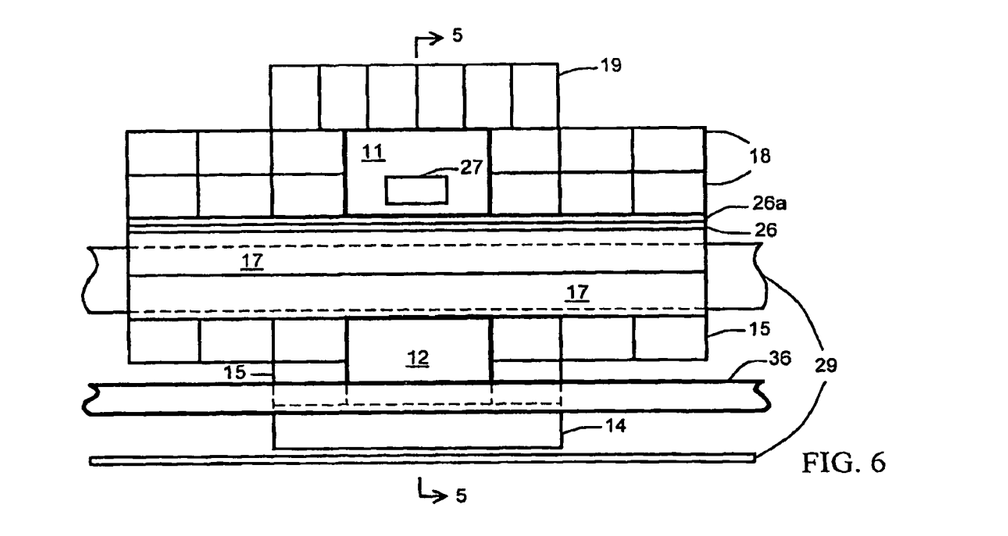
FIG. 6 is a side elevation view showing the disposition of the assembled components in the analyzer of FIG. 4 in an embodiment including one radiation detector box.

The embodiment of FIGS. 4, 5 and 6 is used primarily for analysis of mining materials that have a high Hydrogen content, and is also useful for analysis of materials.

Referring to FIGS. 4, 5 and 6, another embodiment of a bulk material analyzer 40 constructed with an assembly of components according to the present invention includes a radiation source box 11, a radiation detector box 12, a set of stackable structural beams 14, 15, 16, 17, 18, 19, a frame 22, side shields 24 and spacer sheets 26, 26a. In this embodiment, the radiation-source box 11 is disposed above the conveyor belt 29, and the radiation-detector box 12 is disposed below the activation region 30 on the opposite side of the activation region 30 and the conveyor belt 29 from the radiation-source box 11.

Some of the structural beams 15, 16, 17 are disposed between the activation region 30 and the conveyor-support structure 34, 35, 36 when the radiation detector box 12 is disposed below the conveyor belt 29.

In one embodiment, structural beams 18, 19 providing at least 150 mm of borated polyethylene as the radiation shielding material are disposed around the radiation-source box 11 to attenuate the neutrons leaking out of the neutron-emitting region by at least a factor of 8. This embodiment reduces the gammas rays emitted by the conveyor support structure by a factor of at least 8, which is so low that the signature of such emitted gamma rays are not detected in the analysis of the material on the belt.

The structural beams 18, 19 also minimize the neutron flux in a concrete floor above the analyzer 40.

Side shields, such as the side shields 24 in the embodiment of FIGS. 1, 2 and 3, are not included in the embodiment of FIGS. 4, 5, and 6, in which the neutron source box 11 is disposed above the activation region 30 because the trough defining shields 16 normally provide sufficient shielding. Nonetheless, such side shields may be included in an embodiment of a bulk material analyzer in which the neutron source box is disposed above the activation region.

The spacer sheets 26a act as sacrificial materials that can be abraded away by the edge of a misaligned belt and thereby prevent any damage to the radiation source box 11.

In one embodiment, shield extensions 44 made of cowling sheets 46 containing radiation shielding material are optionally attached to the frame 22 adjacent to the open ends of the tunnel 32 and disposed above and to the sides of the conveyor belt 29 to restrict radiation streaming beyond the line of the conveyor belt 29 from the tunnel apertures. The shield extensions 44 essentially lengthen the disposition of radiation shielding material. The shield extensions 44 are relatively lightweight. In one embodiment, the cowling sheets 46 are two-inch thick polypropylene sheets.

Aperture leakage radiation is a problem when making PGNA analyzers shorter and/or lighter. The shield extensions 44 are used with an embodiment of a PGNA bulk material analyzer 40 in which the tunnel 32 is 1800 mm long. In traditional PGNA bulk material analyzers, the tunnel typically has a length in a range of from 2100 to 2400 mm. The shield extensions 44 lower the radiation dosage to anyone walking along the conveyor belt close to the analyzer. The shield extensions 44 are particularly useful for all analyzer utilizing the maximum allowed neutron sources. The shield extensions 44 are essential for wide tunnel applications with large neutron sources.

A preferred embodiment includes a 600-mm long shield extension 44 on both end of an 1800-mm long tunnel of a PGNA analyzer. This enables a source intensity of $2 \times 10^8$ neutrons per second.

The use of such a shield extension with the embodiment of bulk material analyzer shown in and described with reference to FIGS. 1-3 also is optional.

A replaceable steel crash bar 37, such as included in the embodiment described with reference to FIGS. 1-3, is not included in any of the embodiments described herein in which a shield extension, such as shown in FIG. 4, is attached to the frame 22 adjacent to the open ends of the tunnel 32.

Cosmetic side panels 48, 49 are disposed on the upper and lower sides of the analyzer 40.

In other respects, the bulk material analyzer 40 is the same as the bulk material analyzer 10 described above with reference to FIGS. 1, 2 and 3.

The benefits specifically stated herein do not necessarily apply to every conceivable embodiment of the present invention. Further, such stated benefits of the present invention are only examples and should not be construed as the only benefits of the present invention.

While the above description contains many specificities, these should not be construed as limitations on the scope of the present invention, but rather as examples of the preferred embodiments described herein. Other variations are possible and the scope of the present invention should be determined not by the embodiments described herein but rather by the claims and their legal equivalents.

The invention claimed is:

1. An assembly of components for constructing a bulk material analyzer of the type that is used to analyze bulk material transported on a conveyor belt through an activation region located in a tunnel between at least one radiation source and at least one radiation detector within the bulk material analyzer, said assembly comprising:
    a radiation-source box for disposition either above the activation region or below the conveyor belt;
    a radiation-detector box for disposition either below or above the radiation source box on the opposite side of the activation region and the conveyor belt from the radiation-source box; and a set of stackable structural beams predominantly containing radiation shielding material and configured for stacking about the activation region, the radiation-source box and radiation-detector box to prevent unwanted radiation being generated and transported to the radiation-detector box when said boxes are disposed on opposite sides of the activation region and the conveyor belt from each other;

wherein said assembly can be used to construct a bulk material analyzer that can be mounted directly on an existing conveyor support structure, without removing or substantially modifying any part of the existing conveyor support structure.

2. An assembly according to claim 1, wherein the set of structural beams containing radiation shielding material are dimensioned so that at least some of the structural beams can be disposed parallel to the longitudinal axis of the conveyor belt and laterally between the radiation-source box and the conveyor-support structure when the radiation source box is disposed below the conveyor belt.

3. An assembly according to claim 2, further comprising a plurality of side shields of radiation shielding material for disposition outside the conveyor-support structure for reducing neutron fluxes at the sides of the analyzer with respect to the longitudinal axis of the conveyor belt.

4. An assembly according to claim 2, further comprising a frame for supporting the ends of at least some of the structural beams when the beams are so stacked, wherein the frame is adapted for mounting on the conveyor-support structure.

5. An assembly according to claim 1, further comprising a frame for, supporting the ends of at least some of the structural beams when the beams are so stacked, wherein the frame is adapted for mounting on the conveyor-support structure.

6. An assembly according to claim 1, wherein some of the beams are configured for defining a trough adjacent the activation region for supporting the conveyor in a trough-like configuration.

7. An assembly according to claim 6, wherein some of the trough-defining beams define a trough having side walls that are inclined at a first predetermined troughing angle; and wherein some of the tough-dewing beams define a trough having side walls that are inclined at a second predetermined troughing angle that is other than the first predetermined troughing angle.

8. An assembly according to claim 1, further comprising a plurality of spacer sheets of radiation shielding material for disposition between some of the stackable beams for adjusting the height of the tunnel.

9. An assembly according to claim 8, wherein at least some of the spacer sheets are dimensioned for disposition adjacent the edges of the conveyor belt for being contacted by the edges of the conveyor belt when the conveyor belt is significantly misaligned.

10. A bulk material analyzer according to claim 1, wherein the structural beams comprise hollow tubes, which are filled with radiation shielding materials.

11. A bulk material analyzer of the type that is used to analyze bulk material transported on a conveyor belt through an activation region located in a tunnel between at least one radiation source and at least one radiation detector within the bulk material analyzer, said analyzer comprising:

a radiation-source box disposed either above the activation region or below the conveyor belt;

a radiation-detector box disposed either below or above the radiation source box on the opposite side of the activation region and the conveyor belt from the radiation-source box; and a set of stackable structural beams predominantly containing radiation shielding material and stacked about the activation region, the radiation-source box and the radiation-detector box to prevent unwanted radiation being generated and transported to the radiation-detector box; and wherein said bulk material analyzer can, be mounted directly on an existing conveyor support structure, without removing or substantially modifying any part of the existing conveyor support structure.

12. A bulk material analyzer according to claim 11, wherein at least some of the structural beams are disposed parallel to the longitudinal axis of the conveyor belt and laterally, between the radiation-source box and the conveyor-support structure when the source detector box is disposed below the conveyor belt.

13. A bulk material analyzer according to claim 12, further comprising a plurality of side shields of radiation shielding material disposed outside the conveyor-support structure for reducing neutron fluxes at the sides of the analyzer with respect to the longitudinal axis of the conveyor belt.

14. A bulk material analyzer according to claim 12, further comprising a frame supporting the ends of at least some of the stacked structural beams, wherein the frame is mounted on the conveyor-support structure.

15. A bulk material analyzer according to claim 11, further comprising a frame supporting the ends of at least some of the stacked structural stacked, wherein the frame is adapted for mounting on the conveyor-support structure.

16. A bulk material analyzer according to claim 11, wherein some of the beams are configured for defining a trough adjacent the activation region for supporting the conveyor in a trough-like configuration.

17. A bulk material analyzer according to claim 12, further comprising a plurality of spacer sheets of radiation shielding material disposed between some of the stackable beams for adjusting the height of the tunnel.

18. A bulk material analyzer according to claim 17, wherein at least some of the spacer sheets are disposed adjacent the edges of the conveyor belt for being contacted by the edges of the conveyor belt when the conveyor belt is significantly misaligned.

19. A bulk material analyzer according to claim 11 in combination with shield extensions containing radiation shielding material, said shield extensions being disposed adjacent to the open ends of the tunnel above and to the sides of the conveyor belt to restrict radiation streaming beyond the line of the conveyor belt from the tunnel apertures.

20. An assembly according to claim 11, wherein the structural beams comprise hollow tubes, which are filled with radiation shielding materials.

* * * * *

UNITED STATES PATENT AND TRADEMARK OFFICE
CERTIFICATE OF CORRECTION

PATENT NO.        : 8,138,480 B2
APPLICATION NO.   : 12/376839
DATED             : March 20, 2012
INVENTOR(S)       : Raymond John Proctor et al.

It is certified that error appears in the above-identified patent and that said Letters Patent is hereby corrected as shown below:

At column 6, line 27, the "." after "with" should be omitted.

At column 6, line 27, "PCNA" should be --PGNA--.

At column 11, line 42, "tough-dewing" should be --trough-defining--.

At column 12, line 36, "stacked structural stacked" should be --stacked structural beams--.

Signed and Sealed this
Seventh Day of August, 2012

David J. Kappos
*Director of the United States Patent and Trademark Office*